United States Patent [19]

Lecoufle et al.

[11] Plant 4,058

[45] May 31, 1977

[54] ORCHID NAMED TENERIFE

[75] Inventors: Maurice Lecoufle; Michel Vacherot, both of Boissy-St.-Leger, France

[73] Assignee: Les petits-fils et Fils de Vacherot & Lecoufle, Boissy-St.-Leger, France

[21] Appl. No.: 690,253

[22] Filed: May 26, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new variety of orchid plant of the genus Odontioda distinguished particularly by the overall deep red coloration of its flower, the sepals, petals and labellum being generally of a dark geranium lake color slightly darkened in the central parts by a suffusion of magnolia purple giving an impression of a very slightly darker center, with the white anther providing a very small white center appearing above the very small yellow teeth of the labellum, all of which combines with an unusual and radially uniform shape to produce a most attractive flower. The new plant is further distinguished in that it has no definite flowering period and flowers whenever new growth is completed.

1 Drawing Figure

BACKGROUND OF THE NEW PLANT

Our new orchid plant originated as a cultivar of the unpatented variety Odontioda Henriette Lecoufle which resulted from the cross of Odontioda Balek × Odontoglossum Pacha (both unpatented) made by us at Boissy-St.-Leger, France, in the course of breeding efforts carried on since 1956 with the object of producing good cultivars of Odontiodas having improved shape, large size and improved red coloring. The original plant (Oda. Henriette Lecoufle) flowered for the first time in 1959 and our asexual propagation of this cultivar in 1966 by meristem tissue culture flowered the first time in 1971.

Our new plant was selected for propagation because of its distinctive shape and solid red coloring which appeared to be a most favorable realization of our breeding efforts and our continued meristem propagation of this cultivar at Boissy-St.-Leger, France, through successive generations has shown that its distinctive features are firmly fixed and hold true from generation to generation.

DESCRIPTION OF THE DRAWINGS

Our new orchid plant variety is illustrated by the accompanying drawings which show a full color photographic view of a typical flower and a pen-and-ink drawing showing the shape of a typical flower, the color rendition of the flower being as nearly accurate as can be reasonably had by conventional photographic procedures.

DESCRIPTION OF THE NEW PLANT

The following is a detailed description of our new variety of orchid plant with color designations according to The R.H.S. Colour Chart (RHS) published by the Royal Horticultural Society of London, England, in collaboration with the British Colour Council.

THE PLANT

Origin: Seedling from Oda. Henriette Lecoufle (unpatented).

Parentage:

*Seed parent.*—Oda. Balek (unpatented).

*Pollen parent.*—Odm. Pacha (unpatented).

Classification:

*Botanic.*—Odontioda hybrid.

*Commercial.*—Oda. Mericlone.

Form: Herbaceous plant.

Height: Average length of flowering stem — 60 cm.

Bulb:

*Average Size.*—8 cm. high × 4 cm. wide.

*Color.*—Anthocyanins of deep grey-purple appear on the bulbs.

*Number of Bulbs.*—Usually 4 to 5 with leaves on an adult plant.

*Number of Stems Per Bulb.*—Flowers only on the front bulb (or bulbs) which is (or are) the newest one(s) with one stem if the plant is not very strong and two, one on each side, if it is fully developed.

Foliage:

*Number of Leaves.*—On the front bulb, mainly 4 leaves, 2 from the apex, 2 from both sides, plus several embrionic leaves on each side. The other bulbs also have 4 leaves but the old bulbs lose their leaves beginning with the side ones.

*Size of Leaves.*—Length — Apex leaves — 22 cm. to 30 cm. Side leaves — 15 cm. to 25 cm. Width — Apex—3 to 4.5 cm. Sides — 2 to 3.5 cm.

*Petioles.*—Length of attachment to bulb — 5 cm.

*Venation.*—Very light.

*Color.*—Varying from Green 138A-B to 144A-B.

Stems: Diameter — From 4 mm. at base to 2 mm. at end.

THE FLOWER

Blooming Habit: Recurrent. This plant begins to flower whenever the new growth is completed and thereafter flowers regularly late in fall or during winter at the latitude of Paris, France. In more tropical areas, the plant may bloom two or three times a year.

Number of Flowers: Variable — about 10 to 12 on a medium size flowering plant.

Borne: In a racemose manner on a main stem about 60 cm. long, each flower being carried on a pedicel varying in length from about 45 mm. long for the first flower to about 30 mm. long for the last flower.

Spacing on Stem: The first flower occurs about 38 cm. from the base and thereafter the flowers are alternately spaced at: 40 mm. to second flower; 32 mm. to third flower; 30 mm. to fourth flower; 27 mm. to fifth flower; 25 mm. to sixth flower; 20 mm. to seventh flower, etc. After the last flower, the prolongation of the stem without flower is about 7 mm.

Average Size: Large. From 8½ to 10 cm. in diameter, i.e. from tip to tip of the petals and from tip of lateral sepals to tip of dorsal sepal.

Average Dimensions:

*Sepals.*—Lateral: Length — 48 mm.; Width — 34 mm. Dorsal: Length — 40 mm.; Width — 32 mm.

*Petals.*—Length — 45 mm.; Width — 45 mm.

*Labellum.*—Length — 35 mm.; Width — 26 mm. at widest part, 18 mm. at narrow part.

*Gynostemium.*—Length — 18 mm. Spacing of dormant eyes on the stem, below the first flower: 5 cm., 6 cm., 8 cm. and 14 cm.

Shape of Petals: Generally round with small denticulations on the outer parts.

Color:

*Sepals.*—Near 179B, lined and washed with varying greyed-reds and purples, giving an overall effect at a distance of near 180B with a slight suffusion of 186B along center line.

*Petals.*—Near 179B, lined and washed with varying greyed-reds and purples, giving an overall effect at a distance of near 180B with slight suffusion of 186B at center area.

*Labellum.*—Generally near 179B, lined and washed with varying greyed-reds and purples, giving an overall effect at a distance of near 180B changing progressively into Greyed-Purple 186A-B-C toward the base end and margins, the teeth at center being Yellow Orange 21A and the anther white.

Outstanding distinctiveness of our new variety of orchid plant, in addition to its beautiful solid red color and the very unusual shape of the flowers, resides in its good production of flowers on relatively long pedicels, its ability to flower more than once each year, and its strong rapid growth following its first flowering.

We claim:

1. A new and distinct seedling cultivar of orchid Oda Balek × Odm. Pacha, substantially as herein shown and described, characterized as to novelty by the overall deep red color of its flowers and the distinctive flower form which generally conforms with an equilateral rectangular shape.

* * * * *

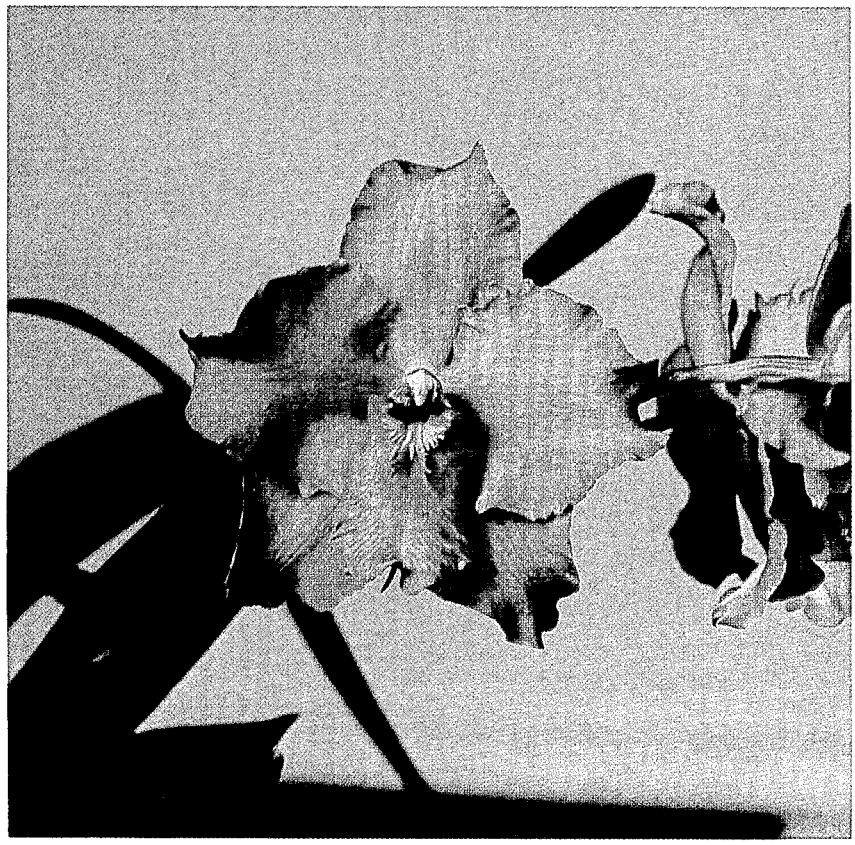
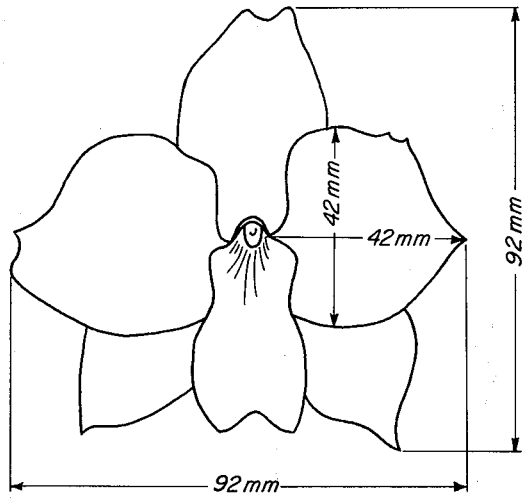
42mm
42mm
92mm
92mm